United States Patent
Gioffre

(10) Patent No.: US 11,083,749 B2
(45) Date of Patent: *Aug. 10, 2021

(54) METHODS AND COMPOSITIONS FOR TREATING SKIN

(71) Applicant: SORPTION THERAPEUTICS, LLC, Ridgefield, CT (US)

(72) Inventor: Anthony Joseph Gioffre, Ridgefield, CT (US)

(73) Assignee: SORPTION THERAPEUTICS, LLC, Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/818,498

(22) Filed: Mar. 13, 2020

(65) Prior Publication Data

US 2020/0215104 A1    Jul. 9, 2020

Related U.S. Application Data

(63) Continuation of application No. 15/114,993, filed as application No. PCT/US2015/012877 on Jan. 26, 2015, now Pat. No. 10,624,922.

(60) Provisional application No. 61/934,023, filed on Jan. 31, 2014.

(51) Int. Cl.
| | | |
|---|---|---|
| *A61K 33/08* | (2006.01) | |
| *A61K 47/06* | (2006.01) | |
| *A61K 9/00* | (2006.01) | |
| *A61K 33/06* | (2006.01) | |
| *A61K 47/02* | (2006.01) | |
| *A61K 47/26* | (2006.01) | |
| *A61K 9/16* | (2006.01) | |
| *A61K 47/34* | (2017.01) | |

(52) U.S. Cl.
CPC ............ *A61K 33/08* (2013.01); *A61K 9/0014* (2013.01); *A61K 9/0019* (2013.01); *A61K 9/16* (2013.01); *A61K 33/06* (2013.01); *A61K 47/02* (2013.01); *A61K 47/06* (2013.01); *A61K 47/26* (2013.01); *A61K 47/34* (2013.01)

(58) Field of Classification Search
CPC ...... A61K 9/0014; A61K 47/02; A61K 33/08; A61K 33/06
See application file for complete search history.

(56) References Cited

U.S. PATENT DOCUMENTS

| | | |
|---|---|---|
| 4,526,583 A | 7/1985 | Gioffre |
| 4,568,343 A | 2/1986 | Leeper et al. |
| 4,592,855 A | 3/1986 | Gioffre et al. |
| 4,627,972 A | 12/1986 | Gioffre et al. |
| 4,795,482 A | 1/1989 | Gioffre et al. |
| 4,808,300 A * | 2/1989 | Yao ........................ C10G 25/03 208/28 |
| 4,826,497 A * | 5/1989 | Marcus .................... B01J 20/18 604/359 |
| 4,826,676 A | 5/1989 | Gioffre et al. |
| 5,084,427 A | 1/1992 | Tsoucalas |
| 5,254,337 A | 10/1993 | Marcus et al. |
| 8,147,855 B2 | 4/2012 | Hahn et al. |
| 2003/0133990 A1 | 7/2003 | Hursey et al. |
| 2007/0237834 A1 | 10/2007 | Gupta |
| 2008/0247979 A1* | 10/2008 | Benjaminson ..... A61K 47/6949 424/68 |

FOREIGN PATENT DOCUMENTS

| | | |
|---|---|---|
| WO | WO2009061575 | 5/2009 |
| WO | WO2010079209 | 9/2010 |
| WO | WO2015116529 | 12/2015 |
| WO | WO2015116529 | 1/2016 |

OTHER PUBLICATIONS

Prestium Pharma, Zonalon (doxepin hydrochloride), 5% Cream Package Insert, Oct. 2014.
Kadaifci, Bijen, Multicomponent Ion Exchange on Zeolite 4A, A Thesis Submitted to the Graduate School of Natural and Applied Sciences of the Middle East Technical University, Nov. 2011; retrieved from https://etd.lib.metu.edu.tr/upload/12613916/index.pdf on May 12, 2018.

* cited by examiner

*Primary Examiner* — Mark V Stevens

(57) ABSTRACT

Methods and compositions are disclosed for treating an area of the skin of a patient, e.g., an itch, insect bite or sting, inflammation, pain or irritation, by applying to said area of the skin an effective amount of a siliceous molecular sieve adsorbent to treat the condition.

6 Claims, No Drawings

METHODS AND COMPOSITIONS FOR TREATING SKIN

CROSS REFERENCE TO RELATED APPLICATIONS

This application is a continuation of U.S. application Ser. No. 15/114,993 filed Jul. 28, 2016 which claims the benefit of priority of U.S. Provisional Application Ser. No. 61/934,023 filed Jan. 31, 2014 each of which is herein incorporated by reference in its entirety.

FIELD OF THE INVENTION

The present invention generally relates to methods and compositions for treating skin, and more particularly to methods and compositions for treating skin wherein the compositions comprise a siliceous molecular sieve adsorbent.

BACKGROUND OF THE INVENTION

Skin is a large and complex body organ. In humans and many animals, it can comprise from about 15 to 20% of the entire body weight. It serves as a protective barrier to environmental toxins and assaults. Conditions on the skin, or conditions in the body, can cause inflammation or irritation, or both, of the skin. Pain is often associated with such conditions. Such conditions may originate from a variety of sources, including, but not limited to, insect bites and stings, e.g., mosquito bites and bee stings, skin irritants, e.g., poison ivy, or conditions of the skin or body, e.g., eczema or arthritis. There are several biological pathways that may contribute to skin inflammation. For example, one immune response of assaulted tissue is histamine release, predominantly by basophilic cells. Another pathway that may contribute to skin inflammation is release of enzymes such as, for example, cyclooxygenase-2 (also referred to as COX-2), an enzyme known to promote inflammation and pain, or phospholipase-2 (PLA-2) by cells and tissue subjected to immune assaults.

For example, the skin contains nerves and highly specific sensory organs that are specialized and disposed so as to differentiate the stimuli leading to such distinct sensations as heat, cold, pressure, pain, itch and the like. In addition to normal sensory stimuli, nerves in the skin are also responsive to native or foreign chemicals such as proteases, prostaglandins, complement-system molecules, allergens, mitogens and the like which may be presented due to tissue injury or environmental exposure. Agents which are effective to combat one source of sensory stimulus—for example steroidal agents to treat skin inflammation—are ineffective against other sensory stimuli such as pressure, heat, or the transitory sting or itch caused by an applied skin care product. Conversely, local anesthetic agents which are effective to depress all sensory or even motor activity in a treated region are not desirable if only a single sensation—for example a transitory sting or itch—is sought to be eliminated. To complicate the situation, the structural matrix of the skin affords a "barrier function" which tends to exclude or inhibit the entry of foreign material, including potentially therapeutic agents.

Typical compositions suitable for topical application to the skin often contain a medicament such as hydrocortisone as their essential active ingredient. Other compositions, such as described, for example in U.S. Pat. No. 8,147,855, granted Apr. 3, 2012, disclose methods for inhibiting sensory responses in the skin such as pain and itch using topical formulations containing aqueous-soluble divalent strontium cation in a suitable topical keratinized skin formulation vehicle. Such a composition may, for example, contain an astringent such as aluminum acetate in a suitable concentration, e.g., 0.2 wt %, and other suitable inactive ingredients, e.g., butylene glycol, caprylyl glycol, dehydroacetic acid, glycine, malic acid, phenoxyethanol, water, and, xanthan gum, and further optionally including other ingredients such as strontium chloride hexahydrate. Other compositions may include an abrasive component such as, for example, ground walnut shells. While these products may be at least partially effective in alleviating symptoms, e.g., itch, they may not be effective in managing the source of the condition, e.g., removal of histamine or enzyme from the affected area of the skin.

Another composition indicated for management of moderate pruritus is one which contains doxepin hydrochloride and has been available, for example, under the trademark ZONALON™ (doxepin hydrochloride) cream, 5%, from Fougera Pharmaceuticals, Inc. In its package insert, under the section entitled "CLINICAL PHARMACOLOGY", it is stated that "Although dopxepin HCL does have H1 and H2 histamine receptor blocking actions, the exact mechanism by which doxepin exerts its antipruritic effect is unknown.".

Accordingly, new methods and compositions are desired for treating conditions on the skin, e.g., itch, insect bite or sting, inflammation, pain or irritation. Further, new methods and compositions are desired for treating conditions on the skin that can remove or eliminate biologic compounds, e.g., histamine or an enzyme, that may contribute to the discomfort associated with the particular condition.

SUMMARY OF THE INVENTION

New methods and compositions are provided for treating conditions on the skin, e.g., itch, insect bite or sting, inflammation, pain or irritation using siliceous molecular sieve adsorbents. Further, new methods and compositions are provided for treating conditions on the skin that can remove biologic compounds, e.g., histamine or an enzyme, that may contribute to the discomfort associated with the particular condition, e.g., inflammation. In addition, new methods and compositions for inhibiting sensory responses in the skin such as pain and itch using topical formulations containing siliceous molecular sieve adsorbents.

By the present invention, it is now possible for patients to obtain relief from discomfort associated with skin conditions, e.g., itch, insect bite or sting, inflammation, pain or irritation. In addition, the present invention provides a unique solution to the problems associate with the presence of biologic compounds that may contribute to the discomfort associated with skin conditions, e.g., e.g., itch, insect bite or sting, inflammation or irritation. In accordance with the present invention, it may be possible to adsorb biologic compounds, e.g., histamine or an enzyme, from an area of the skin that is affected by the condition, e.g., inflammation, which biologic compounds may contribute to a feeling of discomfort in the affected area.

DETAILED DESCRIPTION OF THE INVENTION

Unless otherwise expressly set forth elsewhere in the application, the following terms shall have the following meanings:

The term "patient" includes humans and other mammals.

The phrase "pharmaceutically acceptable" is employed herein to refer to those compounds, materials and compositions within the scope of sound medical judgment, suitable for use in contact with the tissues of human beings and animals without excessive toxicity, irritation, allergic response, or other problem or complication commensurate with a reasonable risk/benefit ratio.

The term "effective amount" means the total amount of the component of interest, e.g., the siliceous molecular sieve adsorbent or a therapeutic agent, that is sufficient to show a patient benefit.

The term "treating" refers to: (i) preventing a disease, disorder or condition from occurring in a patient which may be predisposed to the disease, disorder and/or condition but has not yet been diagnosed as having it; (ii) inhibiting a disease, disorder or condition, i.e., arresting its development; and (iii) relieving a disease, disorder or condition, i.e., causing regression of the disease, disorder and/or condition or relief of symptoms associated with the disease, disorder or condition.

The term "%" or "wt %" means percentage by weight with reference to the total weight of the composition.

The siliceous molecular sieve adsorbents suitable for use in accordance with the present invention include any aluminosilicate molecular sieves having a $SiO_2$ framework, or $SiO_2/Al_2O_3$ framework, that are useful in treating a patient when administered in an effective amount. The siliceous molecular sieves suitably employed in the practice of the invention include the microporous crystalline aluminosilicates, i.e. the zeolitic molecular sieves as well as the silica polymorphs. With respect to the latter compositions, their crystal lattices are ideally formed entirely of $SiO_2$ tetrahedral units, but the as-synthesized forms commonly contain at least trace amounts of aluminum derived from aluminum impurities in the synthesis reagents. The aluminosilicate molecular sieves comprise the large class of well-known crystalline zeolites. These high-silica molecular sieves are either commercially available or are prepared by methods, well-known in the art, involving direct hydrothermal synthesis or involving certain types of crystal lattice dealuminations. A comprehensive review article by E. M. Flanigen concerning both "high" Si/Al zeolites and silica molecular sieves is published in "Proc. 5th Int. Conf. Zeolites, Naples, 1980", L. V. C. Rees, ed., Heyden, London, pp. 760-780. U.S. Pat. No. 4,795,482, issued Jan. 3, 1989, also describes siliceous molecular sieves suitable for use in accordance with the present invention. Suitable siliceous molecular sieves are readily commercially available, e.g., from UOP, Des Plaines, Ill. (USA), and the specific selection of the siliceous molecular sieve can be made by one or ordinary skill in the art of molecular sieve adsorbants. One preferred molecular sieve for use in accordance with the present invention has been commercially available by UOP under the trademark UOP ABSCENTS™ deodorizing powder. Preferably, the siliceous molecular sieves used in accordance with the present invention are manufactured using Current Good Manufacturing Practices such as disclosed by the U.S. Food and Drug Administration ("FDA"), as may be revised from time to time, or similar guidances from other health authorities such as the European Medicines Agency ("EMA"), see for example:
http://www.fda.gov/Drugs/GuidanceComplianceRegulatoryInformation/Guidances/ucm064971.htm Preferably, the siliceous molecular sieves used in accordance with the present invention are crystalline, i.e., not amorphous. However it is noted that particulate materials, e.g., amorphous fused silica, may also be used in the compositions of the present invention, but are distinct from the siliceous molecular sieves.

It is a preferred aspect of the present invention that the adsorptive capacity for water of the siliceous molecular sieve is low in order to avoid the adsorption of moisture and water. It is preferred that the siliceous molecular sieve has capacity for the adsorption of biologic compounds present in the area of the skin that has the particular condition to be treated, e.g., histamine or enzymes. Without wishing to be bound to any particular theory, it is believed that the adsorption of histamine and enzymes that may contribute to the discomfort associated with an inflammation reaction, e.g. cyclooxygenase-2, phospholipase-2, collagenase, elastase, lipooxygenase and phosphodiesterase, can be adsorbed by the siliceous molecular sieves used in accordance with the present invention. Such siliceous molecular sieves are referred to in the art as being hydrophobic or having high hydrophobicity.

The pharmaceutically acceptable carriers suitable for use in accordance invention include any components that do not have a therapeutic effect in treating a patient, e.g., not a siliceous molecular sieve as described herein for use in accordance with the present invention or a drug, e.g., hydrocortisone. Such pharmaceutically acceptable carriers may generally be classified, for example, as oils, waxes, petrolatum or emulsifiers. It is preferred in accordance with the present invention that the pharmaceutically acceptable carriers are substantially non-adsorbable in the siliceous molecular sieve adsorbant, i.e., at least about 90%, more preferably at least about 95% and most preferably at least about 98% of the adsorptive capacity (by weight) of the siliceous molecular sieve adsorbant is not occupied by the pharmaceutically acceptable carriers. Stated another way, preferably less than 10%, more preferably less that 5% and most preferably less that 2% of the adsorptive capacity (by weight) of the siliceous molecular sieve adsorbant is occupied by the pharmaceutically acceptable carriers. Techniques for determining the adsorptive capacity of siliceous molecular sieves and the amount of adsorption of particular components is known to those skilled in the art.

Various examples of components that may be considered for use as pharmaceutically acceptable carriers are described below. The examples are intended to be non-limiting and represent materials that one of ordinary skill in the art may consider for use depending on the particular composition being prepared. The level and species of the carrier are selected according to the compatibility with other components and other desired characteristic of the product. Some routine selection and experimentation is anticipated in the selection of the pharmaceutically acceptable carriers.

The compositions of the present invention may include an aqueous carrier as a pharmaceutically acceptable carrier. Carriers useful in the present invention include water and water solutions of lower alkyl alcohols. Lower alkyl alcohols useful herein are monohydric alcohols having 1 to 6 carbons, more preferably ethanol and isopropanol. Preferably, the aqueous carrier is substantially water. Deionized water is preferably used. Water from natural sources containing mineral cations can also be used, depending on the desired characteristic of the product.

The compositions of the present invention may include a polymer as a pharmaceutically acceptable carrier. Examples include polymers such as crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. Nos. 5,087,445, 4,509,949, 2,798,053, and in CTFA International Cosmetic Ingredient Dictionary, Fourth Edition, Gottschalck and McEwen, 2006. Examples of commercially available carboxylic acid polymers useful herein include the carbomers, which are homopolymers of acrylic acid crosslinked with allyl ethers of sucrose or pentaerytritol. The carbomers are available as the Carbopol™ 900 series from Lubrizol Corporation, Wickliffe, Ohio (e.g., Carbopol™ 954). In addition, other suitable carboxylic acid polymeric agents include copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaerytritol. These copolymers are known as acrylates/$C_{10\text{-}30}$ alkyl acrylate crosspolymers and are commercially available as Carbopol™1342, Carbopol™ 1382, Pemulen TR-1, and Pemulen TR-2, from Lubrizol. Examples of carboxylic acid polymer thickeners useful herein are those selected from carbomers, acrylates/$C_{10}$-$C_{30}$ alkyl acrylate crosspolymers, and mixtures thereof.

Other polymers include crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379, and EP 228,868.

Other polymers include polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the trademark Sepigel 305 from Seppic Inc., Fairfield, N.J. Other polyacrylamide polymers useful herein include multi-block copolymers of acrylamides and substituted acrylamides with acrylic acids and substituted acrylic acids.

A wide variety of polysaccharides may be useful herein. "Polysaccharides" refer to gelling agents which contain a backbone of repeating sugar (i.e., carbohydrate) units. Examples of polysaccharide gelling agents include those selected from cellulose, carboxymethyl hydroxyethylcellulose, cellulose acetate propionate carboxylate, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also possibly useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the trademark Natrosol Plus from Ashland Corporation, Covington, Ky. Other useful polysaccharides include scleroglucans which are a linear chain of (1-3) linked glucose units with a (1-6) linked glucose every three units, a commercially available example of which is Clearogel™ CS11 from MPP inc., South Plainfield, N.J.

Other thickening and gelling agents useful herein include materials which are primarily derived from natural sources. Examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof. Suitable thickening agents can be selected from the group consisting of silicones, waxes, clays, silicas, salts, natural and synthetic esters, fatty alcohols, and mixtures thereof.

Suitable silicones include alkyl siloxane gellants, high molecular weight dimethicones (fluids greater than 1000 millipascal second "mPas"), and high molecular weight alkyl, hydroxyl, carboxyl, amino, and/or fluoro-substituted dimethicones (fluids greater than 1000 mPas). Preferred silicone gellants are described in U.S. Pat. Nos. 5,654,362 and 5,880,210, and include cyclomethicone and dimethicone crosspolymers (e.g., Dow Corning 9040, Dow Corning Corporation, Midland, Mich.).

Waxes can be defined as lower-melting organic mixtures or compounds of high molecular weight, solid at room temperature and generally similar in composition to fats and oils except that they contain no glycerides. Some are hydrocarbons, others are esters of fatty acids and alcohols.

Suitable waxes may be selected from the group consisting of natural waxes including animal waxes, vegetable waxes, and mineral waxes, and synthetic waxes including petroleum waxes, ethylenic polymers, hydrocarbon waxes (e.g., Fischer-Tropsch waxes), ester waxes, silicone waxes, and mixtures thereof. Synthetic waxes include those disclosed in Warth, Chemistry and Technology of Waxes, Part 2, Reinhold Publishing (1956).

Specific examples of waxes include beeswax, lanolin wax, shellac wax, carnauba, candelilla, bayberry, jojoba esters, behenic acid waxes (e.g., glyceryl behenate which is available from Gattifosse Corporation, Paramus, N.J. as Compritol™), ozokerite, ceresin, paraffin, microcrystalline waxes, polyethylene homopolymers, polymers comprising ethylene oxide or ethylene (e.g., long chained polymers of ethylene oxide combined with a dihydric alcohol, namely polyoxyethylene glycol, such as Carbowax available from The Dow Chemical Company, Midland, Mich.; long-chained polymers of ethylene with OH or another stop length grouping at end of chain, including Fischer-Tropsch waxes as disclosed in Warth, supra, at pages 465-469 and specifically including Rosswax available from Frank B. Ross Company, Rahway, N.J. and PT-0602 available from Astor Wax Corporation, Norcross, Ga.), $C_{24\text{-}45}$ alkyl methicones, $C_8$ to $C_{50}$ hydrocarbon waxes, alkylated polyvinyl pyrrolidones (e.g., "Ganex" alkylated polyvinylpyrrolidines available from the Ashland Inc., Covington, Ky.), fatty alcohols from $C_{20}$ to $C_{60}$ (e.g., "Unilins", available from Baker Hughes, Houston, Tex.), and mixtures thereof.

Water dispersible and oil dispersible clays may be useful to provide structure or thickening. Suitable clays can be selected from montmorillonites, bentonites, hectorites, attapulgites, sepiolites, laponites, silicates and mixtures thereof. Suitable water dispersible clays include bentonite and hectorite (such as Bentone EW, LT from Rheox Inc. Hightstown, N.J.); magnesium aluminum silicate (such as Veegum from Vanderbilt Minerals, LLC, Norwalk, Conn.); attapulgite (such as Attasorb or Pharamasorb from BASF Corporation, Florham Park, N.J.); laponite and montmorillonite (such as Gelwhite from BYK-Gardner GMBH, Geretsried, Del.); and mixtures thereof. Suitable oil dispersible clays include organophilically modified bentonites, hectorites and attapulgites. Specific commercially available examples of these clays include Bentone 34 (Rheox Inc.)—Quaternium-18 Bentonite; Tixogel VP (BYK-Gardner)—Quaternium-18 Bentonite; Bentone 38 (Rheox Corp.)—Quaternium-18 Hectorite; Bentone SD-3 (Rheox Inc.)—Dihydrogenated Tallow Benzylmonium Hectorite; Bentone 27 (Rheox Inc.)—Stearalkonium Hectorite; Tixogel LG (BYK-Gardner)—Stearalkonium Bentonite; Claytone 34 (Southern Clay Produxcts, Inc., Gonzales, Ga.) Quaternium-18 Bentonite; Claytone 40 (Southern Clay) Quaternium-18 Bentonite; Claytone AF (Southern Clay) Stearalkonium Bentonite; Claytone APA (Southern Clay) Stearalkonium Bentonite; Claytone GR (Southern Clay) Quaternium-18/Benzalkonium Bentonite; Claytone HT (Southern Clay) Quaternium-18/Benzalkonium Bentonite; Claytone PS (Southern Clay) Quaternium-18/Benzalkonium Bentonite; and Claytone XL (Southern Clay) Quaternium-18 Bentonite. These organophilic clays can be purchased as pre-dispersed organophilic clay in either an oil or an organic solvent. The materials may be supplied in the form of a heavy paste that can be readily dispersed into the formulation.

Other thickening agents include fumed silicas and alkali metal or ammonium halides. Examples of fumed silicas include Aerosil 200, Aerosil 300, and the alkyl-substituted fumed silicas such as Aerosil R-100, 200, 800, and 900 series of materials, available from Evonik Corporation, Parsippany, N.J.

Powders including various organic and inorganic pigments that color the composition or skin may be used. Organic pigments are generally various types including azo, indigoid, triphenylmethane, anthraquinone, and xanthine dyes which are designated as D&C and FD&C blues, browns, greens, oranges, reds, yellows, etc. Inorganic pigments are generally insoluble metallic salts of certified color additives, referred to as lakes or iron oxides. Suitable pigments include those generally recognized as safe, and disclosed by the CTFA (supra). Specific examples are red iron oxide, yellow iron oxide, black iron oxide, brown iron oxide, ultramarine, FD&C Red, Nos. 2, 5, 6, 7, 10, 11, 12, 13, 30 and 34; FD&C Yellow No. 5, Red 3, 21, 27, 28, and 33 Aluminum Lakes, Yellow 5, 6, and 10 Aluminum Lakes, Orange 5 Aluminum Lake, Blue 1 Aluminum Lake, Red 6 Barium Lake, Red 7 Calcium Lake, and the like. Other useful powder materials include talc, mica, titanated mica (mica coated with titanium dioxide), iron oxide titanated mica, magnesium carbonate, calcium carbonate, magnesium silicate, silica (including spherical silica, hydrated silica and silica beads), titanium dioxide, zinc oxide, nylon powder, polyethylene powder, ethylene acrylates copolymer powder, methacrylate powder, polystyrene powder, silk powder, crystalline cellulose, starch, bismuth oxychloride, guanine, kaolin, chalk, diatomaceous earth, microsponges, boron nitride and the like. Additional powders useful herein are described in U.S. Pat. No. 5,505,937.

Powders for absorbing oil are spherical, nonporous particles, more preferably having a particle size less than 25 microns. Examples of some preferred oil absorbing powders are Coslin C-100 (a spherical oil absorber commercially available from BASF Corporation), Tospearl (spherical silica commercially available from Momentive Performance Materials Inc., New Smyrna Beach, Fla.), ethylene acrylates copolymer such as noted above, and SPCAT 12 available from Kobo Products, Inc., South Plainfield, N.J. The powders may be surface treated with one or more agents, e.g., with lecithin, amino acids, mineral oil, silicone oil, or various other agents, which coat the powder surface, for example, to render the particles hydrophobic or hydrophilic. Such treatment may be preferred to improve ease of formulation and stability.

The pharmaceutically acceptable carriers may also include emulsifiers. The hydrophilic-lipophilic balance value of the emulsifier (herein referred to as HLB) is chosen so as to optimally lower the interfacial tension between two phases of significantly different surface tension. For a polar-in-non-polar system, HLB ranges are typically from about 4 to about 8. For a non-polar-in-polar system, HLB ranges are typically from about 12 to about 20. HLB factors are described in Wilkinson and Moore, Harry's Cosmeticology, 7th Ed. 1982, p. 738. and Schick and Fowkes, Surfactant Science Series, Vol. 2, Solvent Properties of Surfactant Solutions, p 607. Exemplary emulsifiers include those disclosed by the CTFA (supra); and Remington's Pharmaceutical Sciences, 15th Ed. 1975, pp. 335-337; and McCutcheon's Volume 1, Emulsifiers & Detergents, 1994, North American Edition, pp. 236-239.

Particularly useful emulsifiers for the present compositions include polydiorganosiloxane-polyoxyalkylene copolymers. Such polymers are described in U.S. Pat. No. 4,268,499. Suitable copolymers of this type are known and many are available commercially. A preferred emulsifier of this type is known by its CTFA designation as dimethicone copolyol. Preferred emulsifiers are further disclosed in U.S. Pat. No. 5,143,722.

Another preferred class of emulsifiers are high molecular weight polymeric emulsifiers such as are effective for stabilizing glycol/polyol-in-hydrocarbon systems (e.g., Arlacel P135 commercially available from Croda Inc., Edison, N.J.).

The compositions hereof may contain one or more co-solubilizers to enhance the formation and stability of the composition. The co-solubilizer is especially useful to bridge compatibility of two materials which are normally incompatible, resulting in the creation of a single, stable phase. Co-solubilizers may therefore be particularly preferred in the single phase electrostatically sprayable compositions described herein. Suitable co-solubilizers are best chosen using a solubility parameter scale as is described in "Solubility: Effects in Product, Package, Penetration, and Preservation," by C. D. Vaughan, Cosmetics and Toiletries, Vol. 103, October 1988. Based on the solubility parameter of two incompatible materials, a third material with a solubility parameter in between that of the two incompatible materials may sometimes be found which is independently compatible with the two incompatible materials. When all three materials are then combined, they may exhibit the properties of a single stable phase, as could be measured, visually for example, via a light microscope. Co-solubilizers can be polar fluids, non-polar fluids, polar aprotic solvents, or amphiphilic materials and are chosen from these broad categories to fit the needs of the two incompatible materials to create a single phase. Particularly useful co-solubilizers include the polydiorganosiloxane-polyoxyalkylene copolymers described, including the polymers described in U.S. Pat. No. 4,268,499, as well as the surfactants disclosed in U.S. Pat. No. 5,143,722.

The compositions of the present invention may include one or more therapeutic agents. The selection, dosage and incorporation of suitable therapeutic agents can be made using sound medical judgment depending on the particular condition desired to be treated. Classes of therapeutic agents include, for example, antifungal agents, antiviral agents, corticosteroids, antibacterial agents, antiseptics, antiparasitics, anti-inflammatory agents, local anesthetics, and anti-itch and irritation-reducing compounds, pharmaceutically acceptable salts; and therapeutically effective combinations thereof. When the compositions of the present invention contain a therapeutic agent, they may be formulated to be dispensed as prescription medicines or as over-the-counter (OTC) products. The manner of dispensing the composition may vary from country to country and will be regulated by the health authority that has jurisdiction, e.g., the EMA or the FDA. In the U.S., the FDA has monographs of approved active ingredients for use in OTC products, i.e., see http://www.fda.gov/downloads/AboutFDA/CentersOffices/CDER/UCM135691.

Although the OTC monographs, in general, provide lists of active ingredients that may be suitable for use in accordance with the present invention, the OTC monographs for external analgesics, skin protectants and sunscreens, for example, provide lists of active ingredients that may be particularly suitable for use in accordance with the present invention. The FDA also provides a database of inactive ingredients that may be employed in drug products, i.e. see http://www.accessdata.fda.gov/scripts/cder/iig/index.Cfm The selection of suitable active ingredients and inactive ingredients that may be suitable for use in accordance with the present invention can readily be determined by one of ordinary skill in the art. It is noted that for purposes of regulatory approval by health authorities, some of the ingredients suitable for use in accordance with the present invention may be classified as inactive ingredients even though they may have functionality in the composition.

Various examples of components that may be considered for use as therapeutic agents are described below. The examples are intended to be non-limiting and represent therapeutic agents that one of ordinary skill in the art may consider for use depending on the particular composition being prepared.

Examples of useful anti-acne actives include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Examples of anti-wrinkle actives or anti-atrophy actives include retinoic acid and its derivatives (e.g., cis and trans); retinol; retinyl esters; niacinamide, and derivatives thereof; sulfur-containing D and L amino acids and their derivatives and salts, particularly the N-acetyl derivatives, a preferred example of which is N-acetyl-L-cysteine; thiols, e.g., ethane thiol; terpene alcohols (e.g., farnesol); hydroxy acids, phytic acid, lipoic acid; lysophosphatidic acid, alpha-hydroxy acids (e.g., lactic acid and glycolic acid), beta-hydroxy acids (e.g., salicylic acid), and skin peel agents (e.g., phenol and the like).

Examples of anti-inflammatory agent that may be added to the compositions of the present invention such as steroidal anti-inflammatory agents, include but are not limited to hydrocortisone and nonsteroidal anti-inflammatory agents. The variety of compounds encompassed by this group are well-known to those skilled in the art. For detailed disclosure of the chemical structure, synthesis, side effects, etc. of nonsteroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974). Suitable anti-inflammatory compounds may include the following: Phellodendron *Amurense* Cortex Extract (PCE) Feverfew (*Tanacetum parthenium*) Ginger (*Zingiber officinale*) Ginko (*Ginko Biloba*) Cotinus (*Cotinus coggygria*) Goji Berry (*Lycium barbarum*) Milk Thistle Extract (*Silybum marianum*) Honeysuckle (*Lonicera japonica*) Basalm of Peru (*Myroxylon pereirae*) Sage (*Salvia officinalis*) Cranberry Extract (*Vaccinium oxycoccos*) Amaranth Oil (*Amaranthus cruentus*) Pomegranate (*Punica granatum*) Yerbe Mate (*Ilex paraguariensis* Leaf Extract) White Lily Flower Extract (*Lilium Candidum*) Olive Leaf Extract (*Olea europaea*) Phloretin (apple extract) Lifenol (Hops: *Humulus lupulus*) Extract Licochalcone (Licorice: *Glycyrrhiza* inflate extract ingredient) Symrelief (Bisabolol and Ginger extract).

Examples of anti-cellulite agents include, but are not limited to, xanthine compounds (e.g., caffeine, theophylline, theobromine, and aminophylline).

Examples of tanning actives include dihydroxy acetone, tyrosine, tyrosine esters such as ethyl tyrosinate and phospho-DOPA.

Examples of skin lightening agents include include kojic acid, arbutin, ascorbic acid and derivatives thereof (e.g., magnesium ascorbyl phosphate or sodium ascorbyl phosphate), and extracts (e.g., mulberry extract, placental extract). Other suitable skin lightening agents are found in PCT Publication No. 95/34280, PCT Application No. 95/07432, PCT Publication No. 95/23780.

Examples skin soothing or skin healing actives include panthenoic acid derivatives (including panthenol, dexpanthenol, ethyl panthenol), aloe vera, allantoin, bisabolol, and dipotassium glycyrrhizinate.

Examples of antimicrobial or antifungal actives include salicylic acid, benzoyl peroxide, glycolic acid, lactic acid, acetyl salicylic acid, hydrocortisone, acetominophen, resorcinol, and mixtures thereof.

Examples of sunscreen actives are described, for example, by Sagarin, et al., at Chapter VIII, pages 189 et seq., of Cosmetics Science and Technology (1972). Suitable sunscreen actives include, for example, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxy-benzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, and mixtures thereof.

Examples of other agents include hydroxy acids, benzoyl peroxide, D-panthenol, octyl methoxycinnimate, titanium dioxide, octyl salicylate, homosalate, avobenzone, carotenoids, amines (e.g., neutrol), astringents such as aluminum aetate, benzalkonium chloride, zinc sulfate, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides, amino acids such as proline, vitamins, lactobionic acid, acetyl-coenzyme A, niacin, riboflavin, thiamin, ribose, electron transporters such as NADH and FADH2, and other botanical extracts such as aloe vera, feverfew, oatmeal and derivatives and mixtures thereof. Examples of vitamins include, but are not limited to, vitamin A, vitamin Bs such as vitamin B3, vitamin B5, and vitamin B12, vitamin C, vitamin K, and different forms of vitamin E like alpha, beta, gamma or delta tocopherols or their mixtures, and derivatives thereof. Examples of hydroxy acids include, but are not limited, to glycolic acid, lactic acid, malic acid, salicylic acid, citric acid, and tartaric acid. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

In one aspect of the invention, the compositions comprise an anti-irritant amount of the strontium cation accompanied (as in the form of a salt) by one or more ionizing anionic species, preferably an acidic anion species such as a chloride, nitrate, or acetate anion, dissolved or dispersed in an appropriate vehicle. Investigations relating have shown that the anti-irritant effects of the cations of the invention can be optimized by suitable selection of the accompanying anionic species (see, e.g., U.S. Pat. No. 8,147,855). Examples of cation-anion pairs include strontium chloride, strontium nitrate, and strontium acetate. The strontium cation may be included in a suitable topical formulation vehicle at a concentration of about 50 to about 1000 millimolar ("mM"), more typically about 100 to about 500 mM, and most typically about 150 to about 300 mM. The appropriate cation concentration can be achieved, for example, using a single strontium salt, or multiple different cation salts may be combined to yield the total desired cation concentration. One possible composition may comprise, for example, in addition to the siliceous molecular sieve, an astringent such as aluminum acetate in a suitable concentration, e.g., 0.2 wt %, and other suitable inactive ingredients, e.g., butylene glycol, caprylyl glycol, dehydroacetic acid, glycine, malic acid, phenoxyethanol, water, and, xanthan gum, and further optionally including other ingredients such as strontium chloride hexahydrate, provided that such inactive ingredients are not substantially adsorbed by the siliceous molecular sieve.

The compositions and methods of the present invention may also be used for temporary relief of minor skin irritations due to a variety of conditions such as, for example, poison ivy, poison oak, poison sumac, insect bites, athlete's foot and rashes caused by soaps, detergents, cosmetics or jewelry Various other materials may also be present in the composition, as known in the art. These include humectants, pH adjusters, chelating agents (e.g., EDTA), fragrances, and preservatives (e.g., parabens). Water or alcohol soluble dyes may also be suitable to use in compositions of the present invention. Examples of dyes suitable for the compositions of the invention include caramel, carmine, fluorescein derivatives, methoxsalen, trioxsalen, azo dyes, anthraquinone dyes, blue azulenes, guajazulene, chamuzulene, erythrosin, bengal rose, phloxin, cyanosin, daphinin, eosin G, cosin 10B, Acid Red 51, Red Dye 4, Red Dye 40, Blue Dye 1, and Yellow Dye 5, or mixtures thereof.

Further examples of the above-described ingredients, as well as examples of other suitable ingredients in topical product formulations, may be found in publications by CTFA (supra) or the International Cosmetic Ingredient Dictionary and handbook, 15$^{th}$ Edition, Micelle Press (2014).

The compositions may be made into a wide variety of product types that include but are not limited to lotions, creams, gels, sticks, sprays, ointments, pastes, foams, powders, mousses, wipes, patches, hydrogels, suppositories, inhalants, film-forming products, skin masks and films. These product types may contain several types of cosmetically acceptable topical carriers including, but not limited to solutions, suspensions, emulsions such as microemulsions and nanoemulsions, gels, solids and liposomes. The following are non-limiting examples of such carriers. Other carriers can be formulated by those of ordinary skill in the art. The compositions of the present invention may be prepared using methodology that is well known by an artisan of ordinary skill.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol (200-600), polypropylene glycol (425-2025), glycerol, 1,2,4-butanetriol, sorbitol esters, 1,2,6-hexanetriol, ethanol, and mixtures thereof.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of suitable emulsifiers include those typically identified as such in the art of personal care and cosmetic formulations.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, powder, or a wipe containing powder).

The compositions may be applied to the area of the skin in need of such treatment according to a suitable treatment regimen, such as a single application or multiple applications, e.g., every month, every week, every other day, every day, twice a day, or more. Thus, the effective amount of the composition may vary depending on the condition being treated. In certain embodiments, the compositions of the present invention may applied to mild wounds or post-surgical sites to facilitate healing, to insect bites, to poison ivy or similar skin conditions, or in general to mitigate itch, irritation or inflammation. The irritation or inflammation may be of external origins caused by ingredients in skin care and cosmetic products such as retinoid and its derivatives, benzyol peroxide, alpha-hydroxy acids and derivatives thereof, salicylic acid, surfactants, natural plant extracts, sunscreen actives, urea, and preservatives, etc. The irritation or inflammation may be of other external origins such as the sun, wind, or shaving. The irritation or inflammation may also be caused by inherent disease conditions such as acne, rosacea, atopic dermatitis, and other disease states, e.g., arthritis. Thus, in accordance with the present invention, it is not necessary that the skin be damaged, infected or irritated in any way. In some cases, the skin may appear to be normal, yet there is pain, inflammation or discomfort in proximity to an area of the skin. Accordingly, the compositions and methods of the present invention may also be effective to alleviate, or treat, pain associated with such conditions. Itch may associated with some of the above-mentioned conditions or others such as, for example, eczema, psoriasis, dermatitis. Itchiness of the skin or other parts of the body, e.g., ears, mouth, tongue, and the like is commonly referred to in the medical field as pruritus. According to the US National Institutes of Health, some 965 studies have been completed or are underway to study pruritis, see, e.g., https://clinicaltrials.gov/ct2/results?term=pruritus Advantageously, the compositions of the present invention may be suitable for use as an alternative treatment, or an adjunctive treatment, to the treatments described in the above-mentioned studies for pruritus. The design and conducting of pre-clinical and clinical trials appropriate for obtaining regulatory approval of the methods and compositions of the present invention can be readily determined by those of ordinary skill in the art.

The specific amounts of each ingredient used in the compositions of the present invention can vary depending on the particular physical form or consistency desired. Typically, the composition comprises from about 0.1 to 99 wt % of the siliceous molecular sieve adsorbent based on the total weight of the composition. Preferably, the composition comprises from about 1.0 to 90 wt % of the siliceous molecular sieve adsorbent based on the total weight of the composition. More preferably, the composition comprises from about 5.0 to 30 wt % of the siliceous molecular sieve adsorbent based on the total weight of the composition. Thus, the effective amount of the siliceous molecular sieve may vary depending on the condition being treated. For instance, in a typical composition, the siliceous molecular sieve will comprise from about 5 to 90 wt %, the pharmaceutically acceptable carrier will comprise from about 10 to 95 wt %, e.g., 5 to 20 wt % emulsifier and 5 to 75 wt % oil, wax or petrolatum, and water will comprise from about 0 to 50 wt %, said percentages based on the total weight of the composition.

In one aspect of the invention, there is provided a composition comprising: (i) a siliceous molecular sieve adsorbent; and (ii) a pharmaceutically acceptable carrier, wherein the composition has a physical form other than a dry, particulate form.

Preferably, the siliceous molecular sieve is an aluminosilicate having a framework $SiO_2/Al_2O_3$ molar ratio greater than 10. Preferably, the siliceous molecular sieve adsorbent has at least about 90 percent of the framework tetrahedral oxide units that are $SiO_2$ tetrahedra, pore diameters of at least 5.5 Angstroms and a capacity for adsorbed water of not greater than 10 weight percent based on the weight of the molecular sieve adsorbant when measured at 25° C. and at a water vapor pressure of 4.6 torr. Preferably, the siliceous molecular sieve has a capacity for adsorbed water of not greater than 6 weight percent. In one aspect of the invention, the siliceous molecular sieve is a silica polymorph. In another aspect of the invention, the siliceous molecular sieve is an aluminosilicate having a framework $SiO_2/Al_2O_3$ molar ratio greater than 35. Preferably, the aluminosilicate has a $SiO_2/Al_2O_3$ molar ratio of from 200 to 500. In another aspect of the invention, the siliceous molecular sieve comprises a mixture of a silica polymorph and an aluminosilicate having a framework $SiO_2/Al_2O_3$ ratio of from 200 to 500. Preferably, the siliceous molecular sieve contains less than 0.2 weight percent alkali metal on an anhydrous basis. Preferably, the siliceous molecular sieve has a particle size of about 1 to 100 microns. More preferably, the siliceous molecular sieve has a particle size of about 1 to 50 microns. Most preferably, the siliceous molecular sieve has a particle size of about 1 to 10 microns.

Preferably, the pharmaceutically acceptable carrier comprises a compound that is substantially non-adsorbable in the siliceous molecular sieve adsorbent. Preferably, the pharmaceutically acceptable carrier comprises a compound that has an effective molecular diameter of at least 5.5 Angstroms. Often, the pharmaceutically acceptable carrier comprises at least one compound selected from an oil, wax, petrolatum or emulsifier. In one aspect of the invention, the pharmaceutically acceptable carrier comprises at least one compound selected from magnesium aluminum silicate, polyoxyethylene lauryl ether, polyoxyethylene monosteatate, polyoxyethylene sorbitan monolaurate, polyoxyethylene sorbitan monooleate, sorbitan monopalmitate, propylene glycol monostearate, sodium borate plus fatty acid, sodium lauryl sulfate, triethanolamine plus fatty acid, isopropyl myristate, cresol, propylparaben, methylparaben, sorbic acid, carbomer, cetyl alcohol, glyceryl monostearate, methylcerlulose, spermaceti, stearyl alcohol and petrolatum.

In one aspect of the invention, the composition has a physical form that is a fluid having a viscosity. Preferably, the viscosity is at least 1 centipoise. More preferably, the viscosity is from about 1 to 100,000 centipoises. In one aspect, the composition has a physical form other than a dry, particulate form.

In one aspect of the invention, the composition has a physical form that is selected from a liquid, oil, emulsion, lotion, gel, cream, paste, ointment, foam, powder, aerosol, inhalant, spray, patch and suppository.

In one aspect of the invention, the composition further comprises a therapeutic agent. In an aspect of the invention, the therapeutic agent is selected from antifungal agents, antiviral agents, corticosteroids, antibacterial agents, antiseptics, astringents, antiparasitics, anti-inflammatory agents, local anesthetics, and anti-itch and irritation-reducing compounds, pharmaceutically acceptable salts; and therapeutically effective combinations thereof.

In one aspect of the invention, the composition further comprises a strontium cation, e.g., strontium chloride hexahydrate.

In one aspect of the invention, there is provided a composition comprising: (i) a siliceous molecular sieve adsorbent; and (ii) a pharmaceutically acceptable carrier, wherein the composition has a physical form other than a dry, particulate form.

In one aspect of the invention, there is provided a composition comprising:
(a) from about 5 to 30 wt % of a siliceous molecular sieve;
(b) from about 10 to 90 wt % of a pharmaceutically acceptable carrier;
(c) from about 5 to 80 wt % of water.

Preferably, the siliceous molecular sieve comprises a combination of a siliceous molecular sieve aluminosilicate having a framework $SiO_2/Al_2O_3$. molar ratio of from about 1 to 10 and a siliceous molecular sieve aluminosilicate having a framework $SiO_2/Al_2O_3$. molar ratio of greater than 10. In one aspect, the pharmaceutically acceptable carrier comprises a combination of petrolatum and polyoxyethylene sorbitan monooleate.

In one aspect of the invention, there is provided a composition comprising:
(a) about 7.5 wt % of a siliceous molecular sieve aluminosilicate having a framework $SiO_2/Al_2O_3$ molar ratio of from about 1 to 10;
(b) about 7.5 wt % of a siliceous molecular sieve aluminosilicate having a framework $SiO_2/Al_2O_3$ molar ratio of greater than 10;
(c) about 44 wt % petrolatum;
(d) about 18 wt % polysorbate-80; and
(e) about 23 wt % water.

In one aspect of the invention, there is provided a method of treating an itch on an area of the skin of a patient comprising applying to said area of the skin a composition comprising: (i) an effective amount of a siliceous molecular sieve adsorbent; and (ii) a pharmaceutically acceptable carrier.

In one aspect of the invention, there is provided a method of treating an insect bite or sting on an area of the skin of a patient comprising applying to said area of the skin a composition comprising: (i) an effective amount of a siliceous molecular sieve adsorbent; and (ii) a pharmaceutically acceptable carrier.

In one aspect of the invention, there is provided a method of treating inflammation in proximity to an area of the skin of a patient comprising applying to said area of the skin a composition comprising: (i) an effective amount of a siliceous molecular sieve adsorbent; and (ii) a pharmaceutically acceptable carrier.

In one aspect of the invention, there is provided a method of treating an irritation on an area of the skin of a patient comprising applying to said area of the skin a composition comprising: (i) an effective amount of a siliceous molecular sieve adsorbent; and (ii) a pharmaceutically acceptable carrier.

In one aspect of the invention, there is provided a method of treating an area of the skin condition comprising applying to said area of the skin an effective amount of a siliceous molecular sieve adsorbent wherein the siliceous molecular sieve is an aluminosilicate having a framework $SiO_2/Al_2O_3$ molar ratio greater than 10 and the skin condition is selected from an itch, insect bite or sting, inflammation, pain or irritation. In one aspect, the siliceous molecular sieve adsorbent is applied as a powder in the absence of a pharmaceutically acceptable carrier. In another aspect, the siliceous molecular sieve adsorbent is applied as a composition comprising: (i) an effective amount of a siliceous molecular sieve adsorbent; and (ii) a pharmaceutically acceptable carrier.

In one aspect of the invention, there is provided a method of treating pain in proximity to an area of the skin of a patient comprising applying to said area of the skin a composition comprising: (i) an effective amount of a siliceous molecular sieve adsorbent; and (ii) a pharmaceutically acceptable carrier.

In one aspect of the invention, there is provided a method of adsorbing a biologic compound from an area of the skin of a patient, comprising applying to said area of the skin a composition comprising: (i) an effective amount of a siliceous molecular sieve adsorbent; and (ii) a pharmaceutically acceptable carrier. In a preferred aspect, the biologic compound is histamine or an enzyme. In a preferred aspect, the enzyme is selected from at least one of cyclooxygenase-2, phospholipase-2, collagenase, elastase, lipooxygenase and phosphodiesterase.

The following examples are provided for illustrative purposes and are not intended to limit the scope of the claimed invention.

Example 1

10 grams of LZ-10 molecular sieve powder and 10 grams of silicate molecular sieve powder (obtained from UOP, Des Plaines, Ill.) were added to a suitable mixing container. To this, 58 grams of petrolatum (Snow White PET USP, available from Penroco Personal Care Products, Karns City, Pa.)) was added. Then, 30 grams of distilled water were added and 24 grams of polysorbate-80 were added. The mixture was blended with a high speed hand mixer until the contents were homogeneous and creamy (approx. 5 mins).

Total weight 132 grams.
% high silica molecular sieve=15.2 wt %
% of Petrolatum=43.9 wt %
% of Water=22.7 wt %
% of Polysorbate=18.2 wt %

Example 2

A composition according to the procedure set forth in Example 1 was applied to an area of the skin on the arm of an adult human patient having a mosquito bite. The bump (swelling) was reduced within minutes and the itch was relieved.

Example 3

A composition according to the procedure set forth in Example 1 was applied to an area of the skin on the ankle of an adult human patient having inflammation from arthritis. The inflammation and pain was noticeably reduced within an hour. Composition was reapplied and the inflammation and pain was fully relieved with four hours.

Example 4

A composition according to the procedure set forth in Example 1 was applied to an area of the skin on the bottom of a foot of an adult human patient within minutes of receiving multiple wasp stings. The pain was reduced immediately and within a half an hour no evidence of swelling or pain was evident.

Example 5

10 grams of LZ-10 molecular sieve powder and 10 grams of silicate molecular sieve powder (obtained from UOP, Des Plaines, Ill.) were added to a suitable mixing container. To this, 58 grams of petrolatum (Snow White PET USP, available from Penroco Personal Care Products, Karns City, Pa.)) was added. Then, 30 grams of distilled water were added and 24 grams of polysorbate-80 were added. The mixture was blended with a high speed hand mixer until the contents were homogeneous and creamy (approx. 5 mins). The composition was transferred to a glass container and placed in boiling water for 20 minutes.
Total weight 132 grams.
% high silica molecular sieve=15.2 wt %
% of Petrolatum=43.9 wt %
% of Water=22.7 wt %
% of Polysorbate=18.2 wt %

Example 6

An adult female patient was receiving allergy shots twice per month during the summer months (May-September) and once per month during the fall (October-December). During each treatment, one injection was administered to the lower back on each side resulting in a total of two injections per treatment. The injections caused severe itchiness and swelling. The patient applied a small amount of the composition of Example 5 to each side of her back immediately after one of the treatments. The itchiness and inflammation were reduced. Relief was observed within minutes of the application. The itchiness was reduced to a level of 0 on a scale of 0-5, with 0 being no discomfort and 5 being severe.

Example 7

An adult female patient awoke one morning with severe pain on the left side of her left foot. It was very difficult to walk. She applied a small amount of the composition of Example 5 and felt some relief. In the afternoon, she applied the composition again and found in a short time that the pain was gone. The pain did not return.

While this invention has been described with an emphasis upon specific aspects, those skilled in the art will recognize that variations in the aspects disclosed may be used and that it is intended that the invention may be practiced otherwise than as specifically described herein. Accordingly, this invention includes all modifications encompassed within the spirit and scope of the invention as defined by the claims that follow. For example, it should be understood that ingredients other than the ones specifically mentioned herein may be used in accordance with the present invention. In addition, alternative process steps or process conditions effective to make the compositions, e.g., different techniques, steps, temperatures, times, and the like, are known to those skilled in the art and may be employed and are intended to be within the scope of the claims which follow.

Where noted above, publications and references, including but not limited to journal articles, contents of web site identified by links, patents and patent applications, cited in this specification are herein incorporated by reference in their entirety in the entire portion cited as if each individual publication or reference were specifically and individually indicated to be incorporated by reference herein as being fully set forth.

What is claimed is:

1. A composition comprising: (i) a hydrophobic, siliceous molecular sieve adsorbent which is an aluminosilicate having a framework $SiO_2/Al_2O_3$ molar ratio greater than 35 and containing less than 0.2 weight percent alkali metal on an anhydrous basis; and (ii) a pharmaceutically acceptable carrier, wherein: (a) the composition has a physical form that is selected from a lotion, gel, cream, or paste; and (b) the siliceous molecular sieve is present in an amount effective to adsorb a biologic compound from an area of the skin of a patient; and wherein compounds present in the pharmaceutically acceptable carrier are substantially non-adsorbable in the siliceous molecular sieve.

2. The composition of claim 1 comprising from about 1.0 to 90 wt % of the siliceous molecular sieve adsorbent based on the total weight of the composition.

3. The composition of claim 2 comprising from about 5.0 to 30 wt % of the siliceous molecular sieve adsorbent based on the total weight of the composition.

4. The composition of claim 1 wherein the siliceous molecular sieve has a capacity for adsorbed water of not greater than 6 weight percent.

5. The composition of claim 1, wherein the pharmaceutically acceptable carrier comprises at least one compound selected from an oil, wax, petrolatum or emulsifier.

6. The composition of claim 1 wherein the biologic compound is selected from histamine, cyclooxygenase-2, phospholipase-2, collagenase, elastase, lipooxygenase and phosphodiesterase.

* * * * *